United States Patent [19] McGinley et al.

[11] Patent Number: 4,833,335
[45] Date of Patent: May 23, 1989

[54] NEUTRON SHIELDED DOOR FOR RADIATION THERAPY ROOMS

[76] Inventors: Patton H. McGinley, 685 Tahoe Cir., Stone Mountain, Ga. 30083; Jeffrey M. Long, 7928 Skipper La., Tallahasse, Fla. 32301

[21] Appl. No.: 73,580
[22] Filed: Jul. 15, 1987
[51] Int. Cl.[4] .............................................. G21F 7/00
[52] U.S. Cl. ............................ 250/518.1; 250/517.1; 250/515.1
[58] Field of Search ............... 250/515.1, 517.1, 518.1, 250/519.1

[56] References Cited

U.S. PATENT DOCUMENTS

| 3,045,120 | 7/1962 | Ohrn | 250/108 |
|---|---|---|---|
| 3,075,909 | 1/1963 | Haass | 204/193.2 |
| 3,114,839 | 12/1963 | Peters | 250/108 |
| 3,256,440 | 6/1966 | Stark | 250/516.1 |
| 3,818,234 | 6/1974 | Atkins et al. | 250/515 |
| 4,090,087 | 5/1978 | Weissenfluh | 250/519 |
| 4,504,739 | 3/1985 | Weissenfluh | 250/519.1 |
| 4,577,356 | 3/1986 | Johenning et al. | 5/450 |
| 4,608,495 | 8/1986 | Jacobson | 250/519.1 |

FOREIGN PATENT DOCUMENTS 62-235597  10/1987  Japan ................................ 250/515.1

Primary Examiner—Carolyn E. Fields
Assistant Examiner—John A. Miller
Attorney, Agent, or Firm—Birch, Stewart, Kolasch, & Birch

[57] ABSTRACT

A neutron shielded door has a hollow interior portion for containing a neutron retarding fluid. This neutron retarding fluid may consist of hydrogen rich compound, such as water, with a dissolved boron compound. This door contains internal baffles for preventing surging of the neutron retarding fluid when the door is opened and closed. The neutron shielded door is contemplated for use with radiation therapy rooms housing medical accelerators and other equipment which generate low levels of neutrons. Ports are provided for the input and drainage of neutron retarding fluid from the door and fluid indicators are provided for permitting determination of the amount of fluid contained in the door.

7 Claims, 1 Drawing Sheet

NEUTRON SHIELDED DOOR FOR RADIATION THERAPY ROOMS

BACKGROUND OF THE INVENTION

1. FIELD OF THE INVENTION

The present invention relates to a door for a treatment room with a medical accelerator which produces x-ray beams used in cancer therapy. This door prevents the escape of neutrons from the room while permitting access to the accelerator.

2. DESCRIPTION OF THE BACKGROUND ART

Various neutron shield are known in the prior art. However, most are expensive to manufacture and can be complicated to use. It is currently the practice in the medical accelerator art to manufacture doors for therapy rooms from relatively expensive materials (such as various plastics with boron or boric acid).

Accordingly, a need in the art exists for a simple and effective neutron shielded door for a room housing an accelerator. This door should be easy to operate and inexpensive to manufacture.

SUMMARY OF THE INVENTION

Accordingly, it is a primary object of the present invention to provide a neutron shielded door for a radition therapy room which is inexpensive to manufacture.

It is another object of the present invention to provide a neutron shielded door which is simple to operate and maintain.

It is a further object of the present invention to provide a neutron shielded door for a room housing an accelerator which will be effective in shielding personnel from low levels of neutrons.

Another object of the present invention is to provide a neutron shielded door which may be incorporated into existing structures or which may be a part of newly constructed rooms for housing accelerators.

Yet another object of the present invention is to provide a neutron shielded door which may be specifically used in conjunction with a high energy medical accelerator used for cancer therapy.

These and other objects of the present invention are fulfilled by providing a neutron shielded door for a radiation therapy room housing an accelerator which discharges neutrons during use, said door comprising a front face, a rear face, two side faces, a top face and a bottom face which define a hollow interior portion, movement means for readily permitting opening and closing of said door to premit access to said accelerator, inlet means for permitting a neutron retarding fluid to be introduced into said interior portion, said fluid deterring the escape of neutrons from said accelerator, and baffle means arranged in said hollow interior portion for preventing surging of said fluid during movement of said door.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilld in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DETAILED DESRIPTION OF THE PREFERRED EMBODIMENTS

Figure 1:
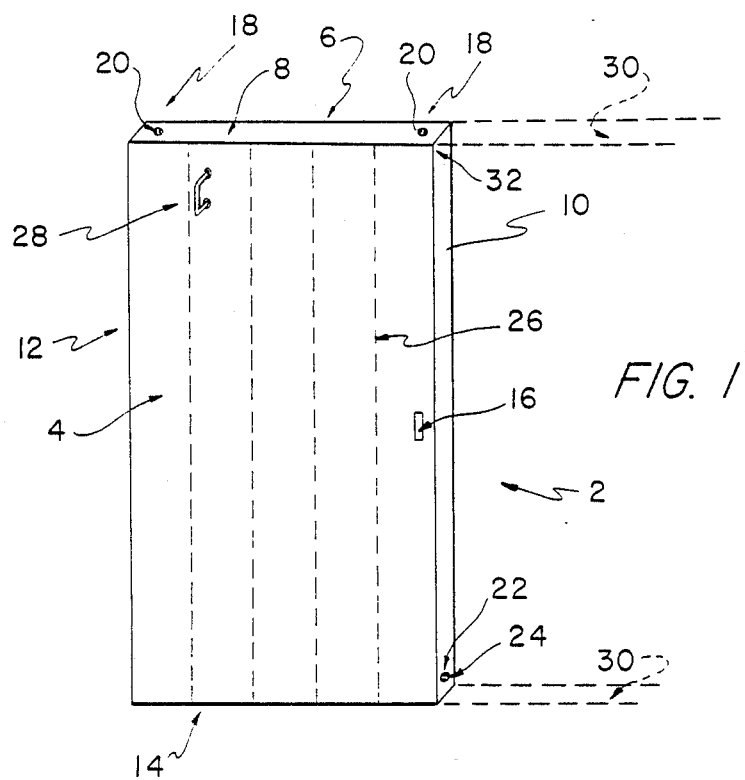
FIG. 1 is a front elevation view of a neutron shielded door of the present invention which slides to permit access to an accelerator.

Referring in detail to the drawings and with particular reference to FIG. 1, a neutron shielded door 2 is disclosed for a radiation treatment room housing an accelerator (not shown). While it is contemplated that the particular accelerator will be a medical accelerator which may be used for instance in cancer therapy, other types of accelerators which are known in the art are equally applicable for use with the neutron shielded door of the instant invention. These accelerators will produce x-ray beams which are contaminated with low levels of neutrons. In order to protect the personnel operating the equipment, it is necessary to provide a neutron shielding door leading to the treatment room.

The neutron shielded door 2 of the instant invention is formed having a front face 4, a rear face 6, a top face 8, two side faces 10, 12 and a bottom face 14. This door may be manufactured from stainless steel or other suitable materials. The door has a hollow interior defined by the various faces. Within this interior, a neutron retarding fluid is held. Two fluid inlets, 18 are provided on the top face 8 of door 2. Fluid inlet plugs 20 are also provided for closing inlets 18. While two inlets are shown, it is contemplated that any configuration of suitable inlets may be used. These inlets 18 permit the neutron retarding fluid to be introduced into the interior of the door. This fluid may be removed from the interior of the door through drain 22 which is normally sealed by drain plug 24. Again, while this drain is shown as being on the bottom portion of side 10, any suitable placement for this plug may be used.

Within door 2, internal baffles 26 are provided which prevent surging of the neutron retarding fluid. Thus, sudden shifting in the center of gravity of the door is prevented when this door is opened or closed. Ease of use of the door is therefore enhanced. The neutron retarding fluid which is held within the door may be any suitable hydrogen rich compound. For instance, it is contemplated that water will be loaded into the door which contains a dissolved boron compound. Thus, the door will satisfactorily operate to provide a neutron capturing arrangement and will protect workers from the low levels of neutrons emitted by the accelerator.

A handle 16 is provided for opening and closing the door. Furthermore, it is contemplated that a latch mechanism (not shown) may be used for assuring that the door remains in a closed, locked position. In order to open and close the door, various arrangements are contemplated. In particular, in FIG. 1, a sliding door arrangement is used. Tracks 30 are provided on a door frame associated with the door whereby door 2 may be slid between an open and closed position. Track followers 32 are indicated for door 2 for permitting this door to slide along track 30. These track followers may be no more than the edge of the door 2 or they may consist of a wheel-type of other bearing arrangement.

Figure 2:
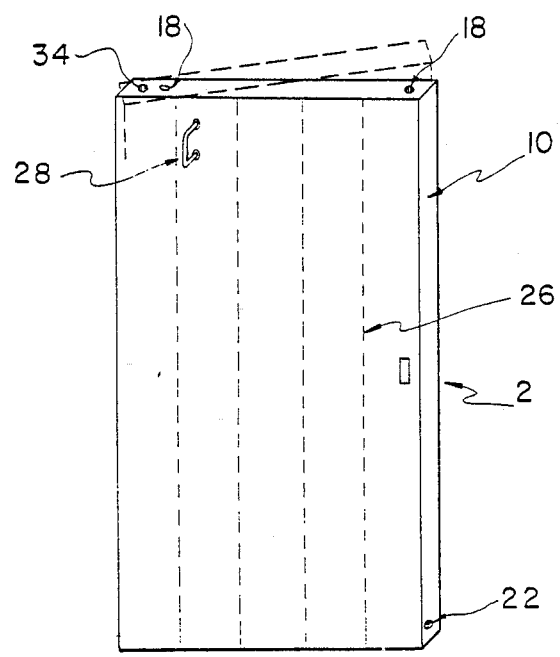
FIG. 2 is a front elevational view similar to FIG. 1 showing the neutron shielded door of the present invention which pivots to permit access to an accelerator.

As seen in FIG. 2, an alternate arrangement for opening and closing the door is contemplated. In this arrangement, door 2 pivots about pivot point 34. A hinge (not shown) is provided for permitting this pivoting of the door. Other arrangements for permitting ready opening and closing of the door are also contemplated as being within the spirit and scope of the instant invention.

On door 2, a fluid indicater 28 is provided. This indicator enables an operator to readily determine the amount of neutron retarding fluid contained in the hollow interior portion of door 2. This fluid indicator may consist of a small water level view port provided near the top of the door. This indicator 28 permits detection of any loss of water by leakage. Other types of indicators such as electronic metering indicators or mechanical fluid level indicators are also contemplated for use with the neutron shielded door of the instant invention.

The neutron shielded door of the instant invention is simple and inexpensive to manufacture yet produces a highly effective neutron shield for a radiation therapy room with an accelerator. This door may be easily maintained and may be incorporated into existing rooms housing accelerators or may be a part of newly constructed rooms for housing accelerators. This door is simple to operate and does not require extensive maintenance.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claim:

1. A neutron shielded door for an enclosure housing an accelerator which discharges neutrons during use, said door comprising:
    a front face, a rear face, two side faces, a top face and a bottom face which define a hollow interior portion;
    movement means for permitting opening and closing of said door to permit access to said accelerator;
    inlet means for permitting a neutron retarding fluid to be introduced into said interior portion, said fluid deterring the escape of neutrons from said enclosure; and
    baffle means arranged in said hollow interior portion for preventing suring of said fluid during movement of said door.

2. The neutron shielded door of claim 1, wherein means are provided for using said door with a medical accelerator.

3. The neutron shielded door of claim 1, wherein said movement means comprises track follower means, said track follower means being guided along a track on a door frame associated with said door to permit sliding of said door relative to said door frame.

4. The neutron shielded door of claim 1, wherein said movement means comprises a hinge for permitting said door to pivot between an open and closed position.

5. The neutron shielded door of claim 1 further comprising a fluid indicator means for indicating the amount of fluid contained in said hollow interior.

6. The neutron shielded door of claim 1 wherein said neutron retarding fluid comprises water with a dissolved boron compound.

7. The neutron shielded door of claim 1, wherein said baffle means comprises a purallity of baffle is longitudinally extending from said top face to said bottom face of said door.

* * * * *